United States Patent [19]

Fourney et al.

[11] 4,127,109
[45] Nov. 28, 1978

[54] SYSTEM OF CONTROLLING ASTIGMATISM DURING CATARACT SURGERY

[75] Inventors: Michael E. Fourney, Malibu; Ronald P. Jensen, Pasadena, both of Calif.

[73] Assignee: Ronald P. Jensen, M.D., Inc., Glendale, Calif.

[21] Appl. No.: 807,197

[22] Filed: Jun. 16, 1977

[51] Int. Cl.² .................................. A61F 09/00
[52] U.S. Cl. ............................ 128/1 R; 128/2 T; 128/335.5; 356/32; 356/397
[58] Field of Search ............ 128/1 R, 2 R, 2 T, 335.5; 356/32, 171

[56] References Cited

U.S. PATENT DOCUMENTS

| | | | |
|---|---|---|---|
| 2,984,147 | 5/1961 | Schoepe et al. | 356/171 |
| 3,194,236 | 7/1965 | Sullivan | 128/335.5 |
| 3,840,015 | 10/1974 | Gain | 128/335.5 |
| 3,949,755 | 4/1976 | Vauquois | 128/335.5 |

Primary Examiner—Dalton L. Truluck
Attorney, Agent, or Firm—W. Edward Johansen

[57] ABSTRACT

The present invention is a system for controlling astigmatism during cataract surgery in which a microscope, having an eyepiece, a tube and an objective lens and having a magnification power of 100 times, is used which includes a length of suture material which is adapted to close a corneal incision and which is cylindrically shaped. The length of suture material has a plurality of parallel lines, which are spaced equally at very close distances in the range of 5,000 to 20,000 lines per inch and which are disposed orthogonally to the longitudinal axis on the cylindrical surface of said length of suture material. When the strain in the length of suture material is in the range of 0.1 percent to 10.0 percent, a reticule is disposed in the microscope adjacent to the objective lens thereof. The reticule measures optically the strain in the length of suture material by comparing a plurality of parallel lines, which are equally spaced at very close distances in the range of 50 to 200 lines per inch, but at a slightly larger spacing than 100 times the line spacing on the length of suture material, and which are aligned optically with the plurality of parallel lines on the length of suture material so that strain may be optically read from the interference formed by the two pluralities of parallel lines.

6 Claims, 8 Drawing Figures

SYSTEM OF CONTROLLING ASTIGMATISM DURING CATARACT SURGERY

BACKGROUND OF THE INVENTION

1. Field of the Invention

The present invention relates to sutures used by ophthalmologists to close corneal incisions and more particularly to a system for determining the tension in sutures in order to control corneal astigmatism.

2. Description of the Prior Art

James P. Gills, opthalmologist, M.D., in his publication, entitled "The Effect of Cataract Sutures on Postoperative Astigmatism", published in Volume 51, February, 1974 issue of the American Journal of Optometry and Physiological Optics on pages 97–100, states that with the advent of microsurgery, cataract wound closure has undergone a great transition. A tight cataract wound closure without flat anterior chamber or iris prolapse is desirable. Control of postoperative astigmatism has importance to those interested in the optical care of aphakic patients. James P. Gills used a Bausch & Lomb keratometer to take preoperative readings and postoperative readings for each patient and he then averaged the readings for each type of suture used in the wound closure. James P. Gills summarized his results with the statement that loose cataract wound closure gave against the rule astigmatism and tight cataract wound closure gave with the rule astigmatism. It is therefore evident that an accurate method of controlling tension in the suture would reduce postoperative astigmatism.

Richard C. Troutman, ophthalmologist, M.D., in his publication, entitled "Microsurgical Control of Corneal Astigmatism in Cataract and Keratoplasty", published in Volume 77, September-October, 1973 issue of the Transactions of the American Academy of Ophthalmology and Otolaryngology on pages OP-563-OP-572, states that in cataract surgery the first goal is to develop an incision and closure which would produce a standard or no deviation of astigmatism from the preoperative level. He also states that cataract incisions closed with silk or catgut suture produced an average of 1.50 D (diopter) astigmatism against the rule. Flattening of the vertical steeper meridian and a corresponding steepening of the flatter horizontal meridian occur in 91% of cases when preoperative and postoperative kerometer measurements are compared. He further states that with microsugically deeply placed monofilament suture in an opposing continuous pattern, corneal keratometer readings can be stabilized to preoperative levels. The purpose of the opposing continuous pattern is to equalize tension within the suture. There is no method in the prior art to determine the relative tension in each stitch.

S. S. Barner, opthalmologist, M.D., in his publication, entitled "Surgical Treatment of Corneal Astigmatism", published in Volume 7, Number 1, Spring, 1976 issue of Ophthalmic Surgery on pages 43–48, states that a quantative surgical keratometer was mounted on an operating microscope in order to visualize changes in corneal curvature by J. L. Barraquer (see V Symposium of International Ophthalmic Microsurgery Study Group, London, 1974). This instrument offers the possibility of reading the amount and axis of astigmatism produced and adjusting the sutures accordingly. A somewhat similar qualitative surgical keratometer was constructed by Richard C. Troutman and described in Volume I of his book *Microsurgery of the Anterior Segment of the Eye*. The Troutman Operating Keratometer identifies the curvatures of the front of the eye, the cornea, during the operation. Prior to the development of the Troutman Operating Keratometer there was no way to monitor the development of surgical procedures during the surgical procedures. The ophthalmologist was only able to measure the curvature of the front of the eye before and after the surgical procedure with a keratometer. This operating keratometer measures qualitatively and not quantatively in that it only measure the variations from the normal standard previously set by the ophthalmologist. The advantage of this operating keratometer over a standard keratometer is that it reads all of the meridians with and against the rule at the same time. It does this by using a reticule placed in the microscope so that the ophthalmologist can compare the difference in all of the meridians in the aspect. I. Robertson in an article in Volume 2, Number 3, 1974, of the Australian Journal of Ophthalmology on page 152 has suggested the use of an illuminated Placido disc mounted on the microscope. The difficulty with both of these methods is that they are basically qualitative instruments and are not easily calibrated so that they reduce postoperative astigmatism. Furthermore the use of a keratometer requires that the ophthalmologist remove the air bubble within the eye before he takes his measurement. The air bubble is essential in keeping the cornea away from the lens which has been implanted.

U.S. Pat. No. 3,994,027, entitled Prepupillary Lens for Implanting in a Human Eye, issued to Ronald P. Jensen and James Fetz on Nov. 30, 1976 teaches a prepupillary lens which may be surgically implanted into a human eye. Similar lenses are discussed in an article by Cornelius D. Binkhorst, M.D., entitled "The Iridocapsular (Two-loop) Lens and the Iris-clip (Four-loop) Lens in Pseudophakia, published in 1973 September-Ocotber edition of Transactions of the American Academy of Ophthalmology and Otolaryngology. All of these lenses require a corneal incision and a corneal wound closure. It would be very beneficial to a patient undergoing a lens implant if the implant surgeon had a tighter control on the tension in each stitch of the suture than he presently has with an operating keratometer.

The inventors have discovered that if the corneal wound closure is too loose the cornea will leak fluids and that if the corneal wound closure is too tight postoperative astigmatism will occur. Since wound closure is dependent on the tension in the stitch of the suture the inventors investigated several methods of measuring the tension. There was one constraint in that they both felt that the measurement of the tension must not interfere with the surgical operation.

SUMMARY OF THE INVENTION

In view of the foregoing factors and conditions characteristic of the prior art it is a primary object of the present invention to provide an optical method of measuring tension in a stitch of suture material.

It is another object of the present invention to provide an optical method of controlling astigmatism during an incision closing procedure wherein the optical method does not interfere with the incision closing procedure.

It is still another object of the present invention to provide an optical method of controlling astigmatism during cataract surgery so that postoperative astigmatism is approximately equal to preoperative astigmatism.

It is yet another object of the present invention to provide a length of suture material that has a diffraction grading thereon which diffracts reflected light to give a color scheme which correlates to the strain and tension in the length of suture material.

It is yet still another object of the present invention to provide an optical method of controlling astigmatism during a corneal incision closing procedure which can be combined with other surgical methods to correct smaller amounts of astigmatism.

In accordance with an embodiment of the present invention, a system for controlling astigmatism during cataract surgery in which a microscope, having an eyepiece, a tube and an objective lens and having a magnification power of 100 times, is used includes a length of suture material which is adapted to close a corneal incision and which is cylindrically shaped. The length of suture material has a plurality of parallel lines, which are spaced equally at very close distances in the range of 5,000 to 20,000 lines per inch and which are disposed orthogonally to the longitudinal axis on the cylindrical surface of said length of suture material. When the strain in the length of suture material is in the range of 0.1 percent to 1.0 percent, a reticule is disposed in the microscope adjacent to the objective lens thereof. The reticule measures optically the strain in the length of suture material by comparing a plurality of parallel lines, which are equally spaced at very close distances in the range of 50 to 200 lines per inch, but at a slightly larger spacing than 100 times the line spacing on the length of suture material, and which are aligned optically with the plurality of parallel lines on the length of suture material so that strain may be optically read from the interference formed by the two pluralities of parallel lines.

The features of the present invention will be more readily appreciated as the same becomes better understood by reference to the following detailed description and considered in connection with the accompanying drawing in which reference symbols designate like parts throughout the figures.

DESCRIPTION OF THE PREFERRED EMBODIMENT

Figure 1:
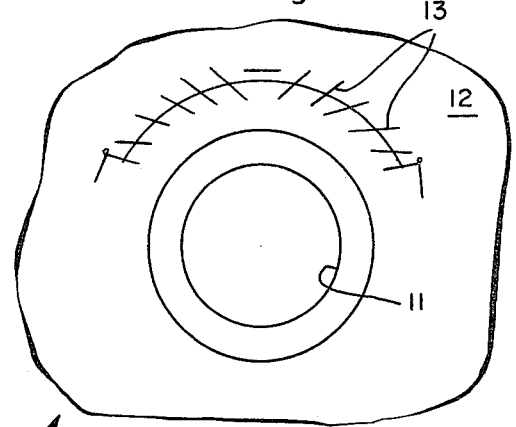
FIG. 1 is a fragmentary plan view of an eyeball that has been sutured after cataract surgery showing the use of stitches of suture material.

In order to best understand the present invention it is necessary to first review the corneal incision closure illustrated in FIG. 1 in which an eyeball 10 is shown having an iris area 11 and scleral area 12. The incision in the scleral area 12 is closed together with a length of suture material 13 by a suturing technique described in Richard C. Troutman's publication discussed in the Description of the Prior Art. In this technique it is critical to control the tension of each stitch of suture material 13.

Figure 2:
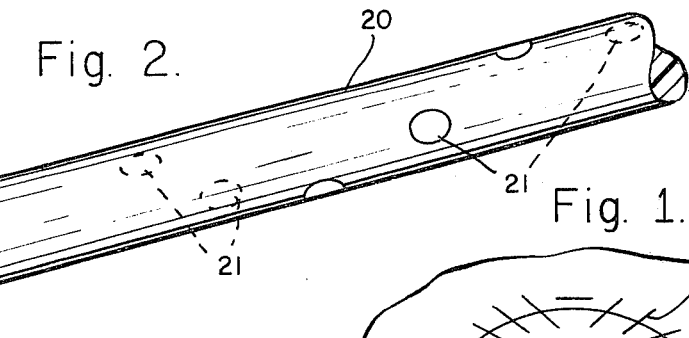
FIG. 2 is a perspective view of a length of suture material which has a diffraction grating placed on its cylindrical surface in accordance with the principles of the present invention.

Referring now to FIG. 2 a perspective drawing of a length 20 of suture material that has a plurality of parallel lines 21 which are equally spaced at very close distances in the range of 5,000 to 20,000 lines per inch disposed orthogonally to the longitudinal axis on the cylindrical surface of the length 20 of suture material. The length 20 of suture material has many sets of the pluralities of such parallel lines 21 arranged sinusoidally and periodicly on its cylindrical surface.

Figure 3:
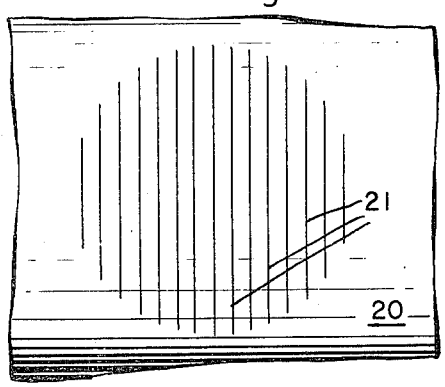
FIG. 3 is a fragmentary plan view of the length of suture material of FIG. 2 which has been greatly enlarged to show a plurality of parallel lines which forms the diffraction grating thereon.

Referring now to FIG. 3 a fragmentary plan view of a plurality of parallel lines 21 indicates the spacing of the parallel lines 21. The suture material is a fine monofilament nylon thread. The parallel lines 21 are placed on the length 20 of suture material a standard technique described in any one of several patents including U.S. Pat. Nos. 3,507,564, 3,578,845, 3,581,280 and 3,617,702. The most direct method of placing these parallel lines 21 on the length 20 of suture material is taught in U.S. Pat. No. 3,588,439, entitled High Resolution Laser Engraving Apparatus, issued to Macy E. Heller and Hendrik J. Gerritsen on June 28, 1971. In this patent a pulsed laser illuminates an entire given area of surface of a member to be engraved with coherent light which varies in relative intensity from point to point over its cross-section in accordance with a predetermined pattern. It has been found that if the absolute intensity and time of duration of the pulse of coherent light are proper, it is possible to obtain engravings in which details of the order of 2 microns in the engraved pattern can be resolved making it possible to not only engrave pictorial patterns, but also hologram patterns.

Figure 4:
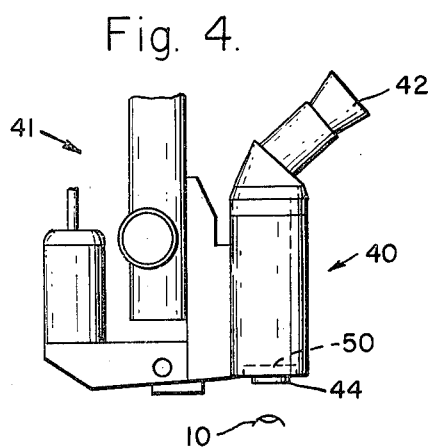
FIG. 4 is an elevational view of a typical microscope used in microsurgery of cataract.

The present invention is a system 40 shown in combination with an operating microscope 41 in FIG. 4. The operating microscope 41 includes an eyepiece 42, a tube 43 and an objective lens 44. The microscope 41 has a magnifying power of 100 times in this combination, although other magnifying powers may be used. The operating microscope 41 has a reticule 50 disposed therein adjacent to the objective lens 44. The length 20 of suture material with the plurality of parallel lines 21 is viewed through the microscope 41.

Figure 5:
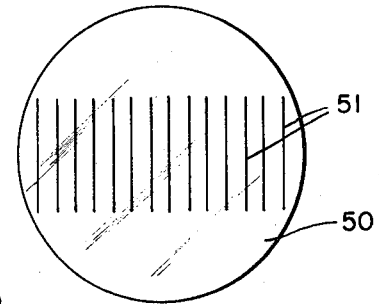
FIG. 5 is a plan view of a first type of reticule used in combination with the microscope according to the principles of the present invention.

In FIG. 5 a plan view of the reticule 50 shows that it has a plurality of parallel lines 51 which are equally spaced at very close distances in the range of 50 to 200 lines per inch, but at a slightly larger spacing than 100 times the line spacing of length of suture material 20.

Figure 6:
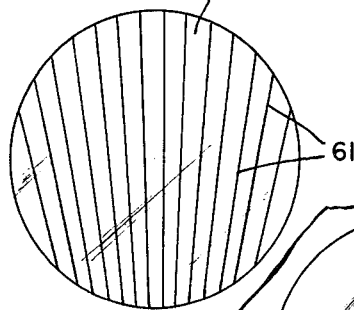
FIG. 6 is a plan view of a second type of reticule used in combination with the microscope according to the principles of the present invention.

In FIG. 6 a plan view of another reticule 60 shows that it has a plurality of substantially parallel lines 61 which are equally spaced at very close distances in the range of 50 to 200 lines per inch at one side and which spread out from the middle line 62 thereof to form a fan-shaped array of lines 61 at a spacing in the range of 100 times the line spacing of the parallel lines 21 of the length 21 of suture material.

Figure 7:
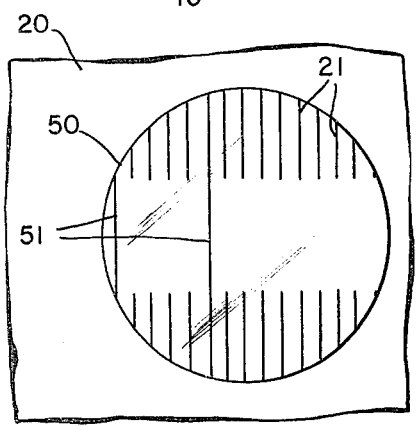
FIG. 7 is a schematic drawing of the vernier pattern formed by the parallel lines of the length of suture material with the reticule of the first type.

In FIG. 7 a schematic drawing of the interference pattern formed on the objective lens 44 by the lines 51 of the reticule 50 and the lines 21 on the length 20 of suture material illustrates a vernier-type method of measuring strain and tension in the length 20 of suture material. Reference to *Moire Analysis of Strain* by A. J. Durelli and V. J. Parks, 1970, on page 280, Chapter 16, Section 16.5, entitled Moire Vernier for the Measurement of the Shifting Distance of the Master Grating is useful in fully explaining the optics of this method.

Figure 8:
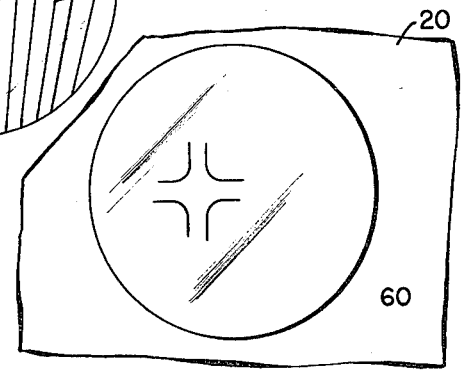
FIG. 8 is a schematic drawing of the Moire pattern formed by the parallel lines of the length of suture material with the reticule of the second type.

In FIG. 8 a schematic drawing of the interference pattern 80 formed on the objective lens 44 by the lines 61 of the reticule 60 and the lines 21 on the length 20 of suture material illustrates a superposition-type method of measuring strain and tension in the length 20 of suture material. Again reference to *Moire Analysis of Strain*, on pages 67-69, Chapter 2, Section 2.3, entitled Superposition of Equidistant Straight Lines on Equiangular Straight Lines is useful in fully explaining the optics of this method. At the point where the star pattern is formed relative to the edge of the reticule 60 is a direct measurement of strain.

The reticules 50 and 60 may be calibrated by using a keratometer or they may be marked with equally spaced lines representing increments of strain in the length 20 of suture material. These two techniques are best suited if the strain is in the range of 0.1 percent to 10.0 percent. The inventors have reason to believe that the strain may be in the range of 5.0 percent to 15.0 percent. In the larger strain range a third technique has also been developed wherein a light source is directed at the diffraction grating formed by the parallel lines 21 on the length 20 of suture material at an angle in the range of 30° to 60° from the microscope 41 and the diffracted light is captured by a light stop on the objective lens 44 of the microscope 41 and seen by the operating surgeon. The diffracted light's color may be correlated with the strain in the length 20 of suture material.

Reference to *Microsurgery of the Anterior Segment of the Eye*, by Richard C. Troutman, M.D., F.A.C.S., Volume I, Introduction and Basic Techniques illustrates the uses of operating keratometers and their importance. The advantage of this system for determining strain in the suture is that it is compatible with other techniques of controlling postoperative astigmatism.

Although nylon suture material is generally used in microsurgery of the eye, this invention is not limited to any one type of suture material. From the foregoing it can be seen that a method for encoding a suture has been described. The encoding of the suture may be done by a pulsed-laser or any method of embossing a plurality of fine parallel lines on a length of suture material. Furthermore any optical technique of reading the change in spacing of these parallel lines is acceptable for this invention. Once the strain and tension data is obtained it must be correlated to the astigmatism changes.

Accordingly it is intended that the foregoing disclosure and showing made in the drawing shall be considered only as an illustration of the present invention. Furthermore it should be noted that the sketches are not drawn to scale and that distances of and between the various figures are not to be considered significant. The invention will be set forth with particularity in the appended claims.

What is claimed is:

1. An improved system for controlling astigmatism during cataract surgery in which a microscope, having an eyepiece, a tube and an objective lens, is used, said improved system comprising:

a. a length of suture material adapted to close a corneal incision, said length of suture material being cylindrically shaped and having a plurality of parallel lines, which are equally spaced at very close distances in the range of 5,000 to 20,000 lines per inch, disposed orthogonally to the longitudinal axis on the cylindrical surface of said length of suture material; and b. means for detecting and measuring optically the strain in said length of suture material in the range of 0.1 percent to 25.0 percent, said means being optically coupled to the microscope.

2. An improved system for controlling astigmatism during cataract surgery according to claim 1 wherein said plurality of parallel lines are enclosed in a plurality of small circular envelopes which are distributed periodically on the cylindrical surface of said length of suture material and sinusoidally thereon.

3. An improved system for controlling astigmatism during cataract surgery according to claim 1 wherein said means for detecting and measuring optically the strain in said suture is a reticule having a plurality of parallel lines, which are equally spaced at very close distances in the range of 5,000 to 20,000 lines per inch, but at a slightly larger spacing than the line spacing on said length of suture material, and being disposed in the microscope adjacent to the objective lens thereof so that said plurality of parallel lines on said reticule are optically aligned with said plurality of parallel lines on said length of suture material in order that strain may be optically read from the interference formed by said two pluralities of parallel lines.

4. An improved system for controlling astigmatism during cataract surgery according to claim 1 wherein said means for detecting and measuring optically the strain in said suture is a reticule having a plurality of lines, which are equally spaced at very close distances in the range of 5,000 to 20,000 lines per inch and which are spaced equally to the spacing of said length of suture material at one end and at a slightly larger spacing than the line spacing of said length of suture material at the other end so that said plurality of lines on said reticule are optically aligned with said plurality of parallel lines on said length of suture material in order that strain may be read optically from the interference formed by said two pluralities of lines.

5. An improved system for controlling astigmatism during cataract surgery according to claim 1 wherein said means for detecting and measuring optically the strain in said suture is a source of white light which is directed at the diffraction grading formed by said plurality of parallel lines on said length of suture material with the diffracted light that is seen through the microscope being correlated with strain in said length of suture material.

6. An improved system for controlling astigmatism during cataract surgery according to claim 1 where the combination of the eyepiece and the objective lens of the microscope magnifies said length of suture material 100 times and said means for detecting and measuring optically the strain in said length of suture material is a reticule having a plurality of parallel lines, which are equally spaced at very close distances in the range of 50 to 200 lines per inch, but at a slightly larger spacing the line spacing on said length of suture material, and being disposed in the microscope adjacent to the objective lens thereof so that said plurality of parallel lines on said reticule are optically aligned with said plurality of parallel lines on said length of suture material in order that strain may be optically read from the interference formed by said two pluralities of parallel lines.

* * * * *